United States Patent [19]
Parker

[11] Patent Number: 6,149,603
[45] Date of Patent: Nov. 21, 2000

[54] METHOD AND APPARATUS FOR DETERMINING WHETHER AN INTUBATED PATIENT HAS BEEN PROPERLY INTUBATED

[75] Inventor: Frederick A. Parker, Gwynedd Valley, Pa.

[73] Assignee: Ventrex, Inc., Horsham, Pa.

[21] Appl. No.: 09/329,366

[22] Filed: Jun. 10, 1999

Related U.S. Application Data
[60] Provisional application No. 60/134,195, May 14, 1999.

[51] Int. Cl.⁷ .................................................. A61B 5/08
[52] U.S. Cl. .................. 600/532; 604/100; 128/200.24; 128/200.26; 128/202.22; 128/207.14
[58] Field of Search ..................................... 600/529, 532; 128/200.24, 200.26, 202.22, 205.23, 207.15, 207.14; 604/100

[56] References Cited

U.S. PATENT DOCUMENTS

| | | |
|---|---|---|
| 2,136,236 | 11/1938 | Draper ..................................... 128/203 |
| 4,572,208 | 2/1986 | Cutler et al. ............................. 128/718 |
| 4,728,499 | 3/1988 | Fehder ....................................... 422/56 |
| 4,879,999 | 11/1989 | Leiman et al. ...................... 128/207.14 |
| 4,928,687 | 5/1990 | Lampotang et al. ............... 128/207.14 |
| 5,156,159 | 10/1992 | Lampotang et al. .................... 128/719 |
| 5,166,075 | 11/1992 | Fehder ....................................... 436/133 |
| 5,179,002 | 1/1993 | Fehder ....................................... 435/56 |
| 5,487,731 | 1/1996 | Garth et al. ......................... 604/100 X |
| 5,648,451 | 7/1997 | Sashida et al. .......................... 528/353 |
| 5,749,358 | 5/1998 | Good et al. .......................... 128/205.23 |
| 5,885,248 | 3/1999 | Denton ................................. 604/100 X |

*Primary Examiner*—John P. Lacyk
*Assistant Examiner*—Ryan Carter
*Attorney, Agent, or Firm*—Jim Zegeer

[57] ABSTRACT

Method and apparatus for indicating proper placement of an endotracheal tube in the trachea of a patient which comprises measuring the oxygen concentration of inspired and expired air and, utilizing this information, performs the calculation necessary to determine whether the tube has been properly placed.

7 Claims, 3 Drawing Sheets

METHOD AND APPARATUS FOR DETERMINING WHETHER AN INTUBATED PATIENT HAS BEEN PROPERLY INTUBATED

REFERENCE TO RELATED APPLICATION

The present application is the subject of provisional application Ser. No. 60/134,195 filed May 14, 1999.

BRIEF DESCRIPTION AND BACKGROUND OF THE INVENTION

The present invention relates to a method and apparatus for determining whether an intubated patient has been properly intubated.

There have been numerous techniques developed for detecting accidental esophageal intubation (see Pat. Nos. 4,879,999, 4,572,208, 4,728,499, 5,166,075, 5,179,002, 5,648,451, 5,749,358, 4,928,687, 5,156,159, and 2,136, 236). For the most part, these patents deal with devices and methods for indicating proper placement of an endotracheal tube by detecting (colorimetry) the presence of carbon dioxide in expired air passing through the device. If the patient has ingested a carbonated beverage prior to intubation, esophageal $CO_2$ may be present and cause misleading indication of the position of the tube.

The present invention determines whether or not an intubated patient has been properly intubated (i.e., whether the tube is in the trachea or incorrectly in the esophagus) by measuring the $\Delta pO_2$ between the inspired and expired gases.

When breathing air, a person uses about one quarter of the oxygen he or she inspires. When breathing oxygen enriched gas they use a correspondingly smaller percentage, but there is still a substantial signal to work with. Rather than just measure the absolute difference in the level of oxygen, between inspired and expired, it would be preferable to measure the derivative, i.e. the differential $dpO_2/dt$, and more preferable, the second derivative, i.e. change in slope instead of, or in addition to, the absolute difference in oxygen content. However, it should be understood that this is not a limiting feature on the broad aspects of the invention.

The measurement(s) will be displayed on a visual display or by an audible annunciator or by both. The display could comprise one LED illuminating at the inflection point when the slope changes positively and a second LED illuminating at the inflection point when the slope changes negatively, thereby obtaining a breath-to-breath indication. Additional measurements may also be made, as already mentioned, of the absolute level (tension or partial pressure) of the inhaled and exhaled gas in order to provide additional information which may be needed to reliably determine whether oxygen is being used by the patient. These measurements may be necessary, particularly during transient conditions, should oxygen be added to the inspired gas.

Thus, the objective of the invention is to provide an improved method and apparatus for determining whether an intubated patient has been properly intubated.

DESCRIPTION OF THE DRAWINGS

The above and other objects, advantages and features of the invention will become more apparent when considered with the accompanying specification and following drawings wherein.

DETAILED DESCRIPTION OF THE INVENTION

Figure 1:
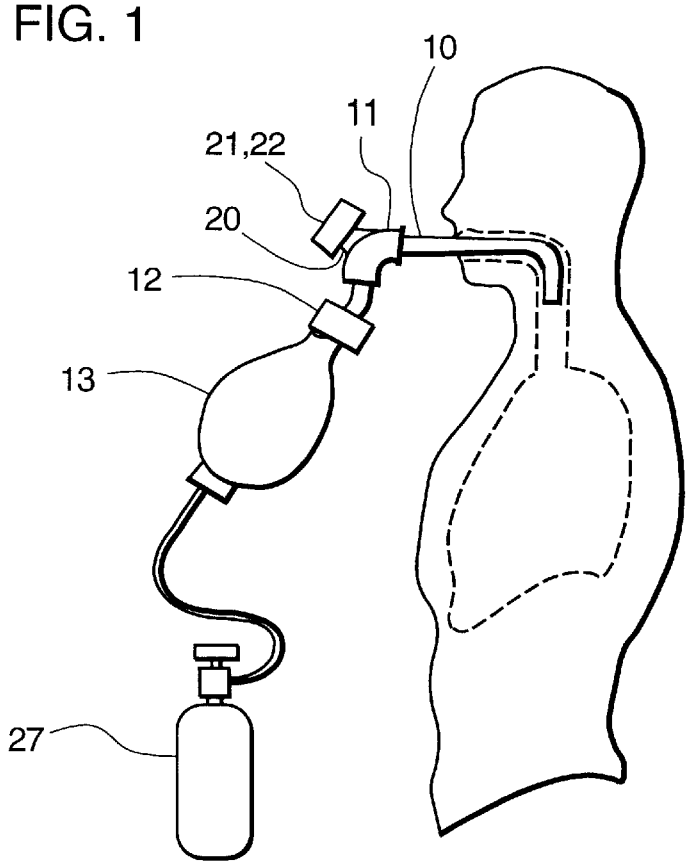
FIG. 1 is a diagrammatic illustration of the device incorporating the invention as applied to a patient.
Figure 2:
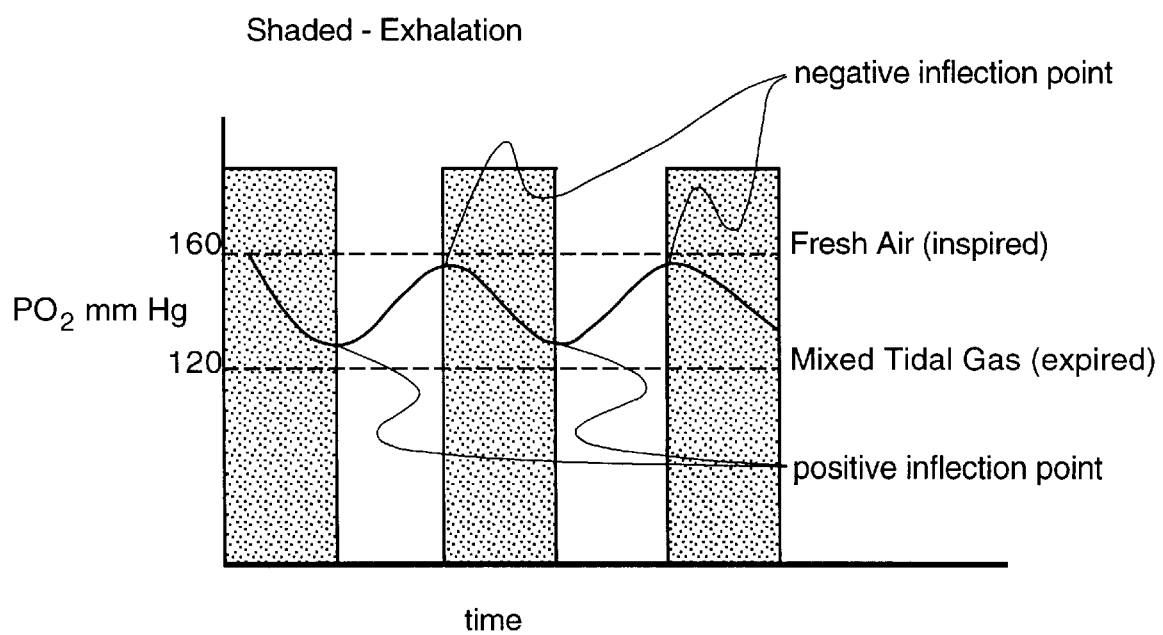
FIG. 2 is a graph of $PO_2$ in millimeters of mercury plotted against time with the shaded portion showing the exhalation and unshaded portion showing inhalation.

Referring to FIG. 1, the endotracheal tube 10 is coupled through a disposable Tee 11 and flow control valves 12 to a squeeze bag 13. An optional source of oxygen 27, to enrich the level administered to the patient is also shown. The detection apparatus according to the present invention includes an oxygen sensor 20 which is detachable from disposable Tee 11, coupled to a processor 21 and display 22. In practice, fresh air, or oxygen enriched gas, goes into the patient's lungs through the Tee 11 to which is attached the oxygen sensor instrument of the present invention and the exhaled or expired gas also comes back through the Tee. The Tee 12 can be disposable and contain a high-efficiency bacterial/viral filter 23 (see FIG. 3) to protect the detachable $O_2$ sensor, processor 21 and display 22 package from patient contamination.

Figure 3:
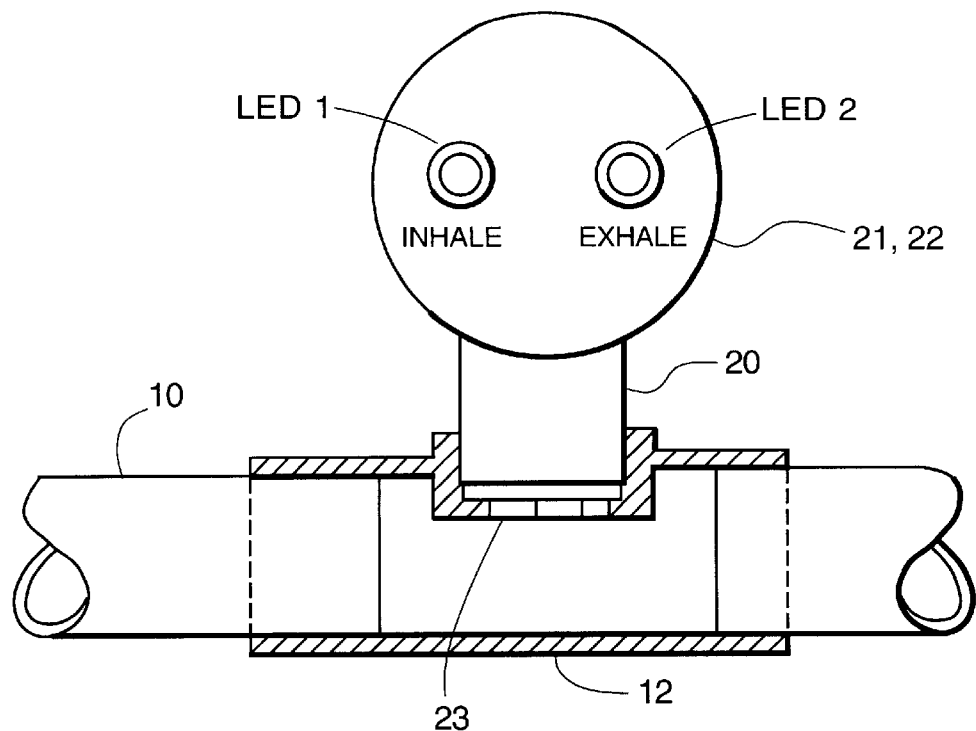
FIG. 3 is a sectional view showing how the disposable Tee connects to the sensor and display and where the high-efficiency filter is installed.
Figure 4A:
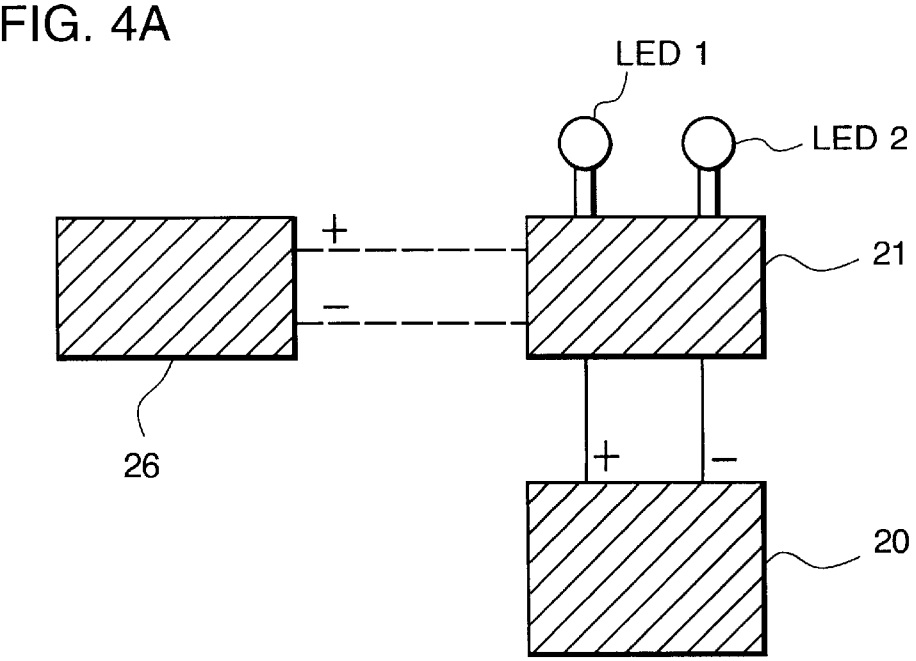
FIGS. 4A and 4B are functional block diagrams of the circuit incorporating the invention.

The electronics (FIG. 4A) include a microprocessor 21 which would illuminate LED 1 during inhalation and LED-2 during exhalation as shown in FIG. 3. The microprocessor 21 causes the LEDs to flash when oxygen sensor 20 output changes from increasing to decreasing, and flash when sensor 20 output changes from decreasing to increasing (due to increase and decrease of either the oxygen concentration or the oxygen partial pressure). In practice, a test switch (momentary actuation) and a green test LED (not shown), may be added which would indicate that the sensor output was correct, that the electronics are operating satisfactorily and that the battery 26 voltage was adequate.

Optionally, a red LED and/or an audible alarm, signaling that there is a problem of some sort, can be included.

Figure 4B:
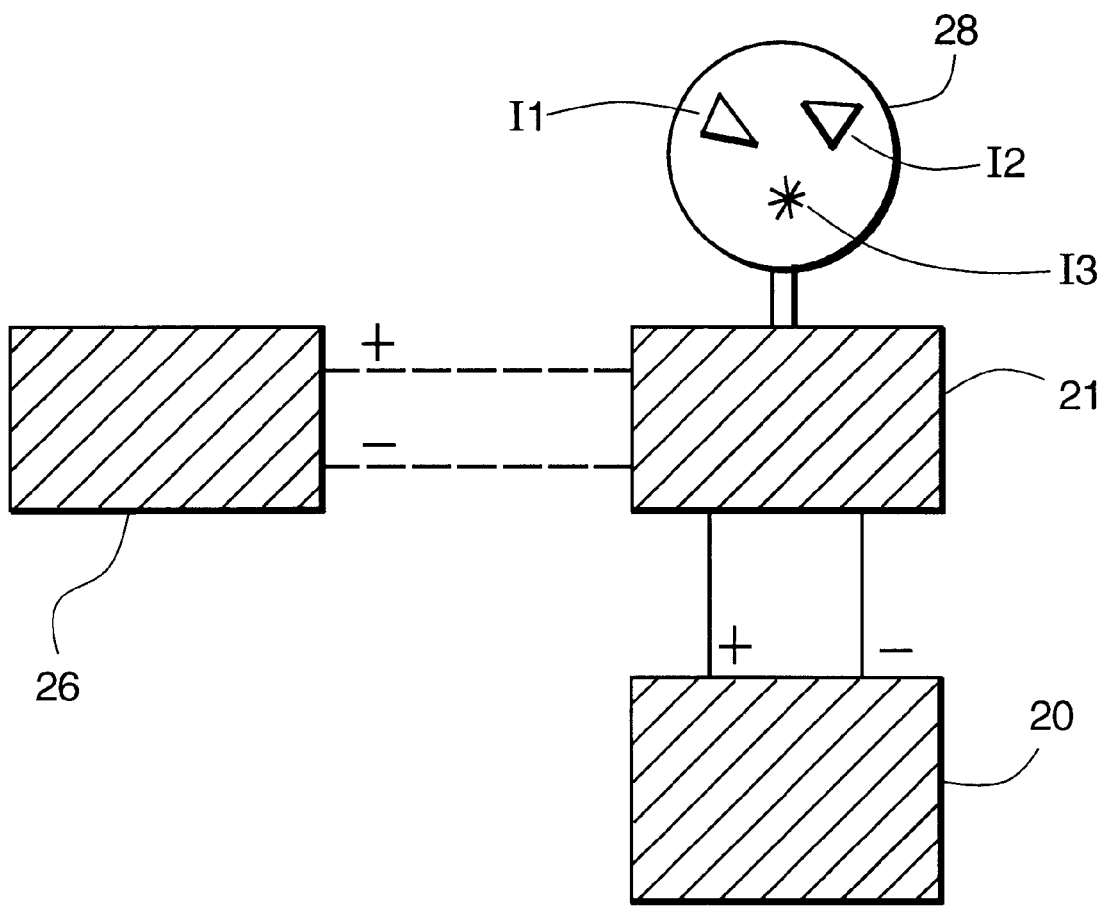

FIG. 4B shows an embodiment wherein the output includes an LCD display 28 with icons $I_1$ and $I_2$ representing inhalation and exhalation, respectively, and icon $I_3$ representing an alarm condition.

In a further embodiment, a single indicator light would be driven to flash when the oxygen level increases and flash again when the oxygen level decreases. In a further embodiment, a single indicator light could be driven only once per breath.

Still another display could consist of an LCD display which could present various icons or textual messages, or both, to convey the desired information.

In addition to the above features others can be added such as an alarm which monitors the inspired oxygen level and signals a decrease due, for example, to the oxygen source being depleted.

While preferred embodiments of the invention have been shown and illustrated and described, it will be appreciated that other embodiments, adaptations and modifications of the invention will be readily apparent to those skilled in the art:

What is claimed is:

1. An endotracheal placement detection (EPD) device for a tubular member (an endotracheal tube), one end of said endotracheal tube adapted for insertion into a patient's trachea and the other end located external to the patient, the detection device comprising: a tubular housing including a multi-legged Tee member coupled to said other end of the endotracheal tube, a second leg of said Tee being coupled to a source of breathing gas, and the third leg of said Tee being coupled to an oxygen sensor, a disposable filter positioned between said oxygen sensor and said Tee, said oxygen sensor including a display for displaying the existence of a difference in oxygen level in gases inspired and expired by said patient and means to indicate any difference.

2. The EPD device defined in claim 1 wherein said oxygen sensor is detachable from said Tee member.

3. A method of indicating proper placement of an endotracheal tube in the trachea comprising measuring the difference in oxygen concentration of inspired and expired air (gas) and indicating any difference between them.

4. The method defined in claim 3 wherein the difference is indicated by determining the rate of change in oxygen concentration between inspired and expired gases.

5. The method defined in claim 3 wherein the difference is indicated by identifying a change in slope between the inspired and expired air (gas).

6. The method of claim 3 having a means to indicate a drop in inspired $O_2$ levels.

7. The method of claim 3 which, in addition to measuring the difference in the oxygen concentration of inspired and expired gas, also measures the rate of change of these levels, from breath to breath, and uses these calculations to determine the significance of the measured difference between the oxygen concentration of the inspired and expired gas.

* * * * *